United States Patent [19]

Karrakussoglu

[11] 4,353,692

[45] Oct. 12, 1982

[54] ORTHODONTIC APPLIANCE

[76] Inventor: Stefanos Karrakussoglu, 1313 S. Finley Rd., Lombard, Ill. 60148

[21] Appl. No.: 187,361

[22] Filed: Sep. 15, 1980

[51] Int. Cl.³ .............................................. A61C 7/00
[52] U.S. Cl. ...................................... 433/16; 433/12
[58] Field of Search .............................. 433/16, 13, 12

[56] References Cited

U.S. PATENT DOCUMENTS

| | | | |
|---|---|---|---|
| 2,908,974 | 10/1959 | Stifter | 433/16 |
| 3,421,221 | 1/1969 | Silverman et al. | 433/8 |
| 4,200,980 | 5/1980 | Johnston | 433/8 |
| 4,243,387 | 1/1981 | Prins | 433/16 |

Primary Examiner—Robert Peshock

Attorney, Agent, or Firm—Emrich, Lee, Brown & Hill

[57] ABSTRACT

The arch wire of an orthodontic appliance is received in the channel of a bracket fixed to each of a patient's teeth to be repositioned. Each bracket includes a holder in which is removably located a selected one of a set of channel members, the channels of which are differently inclined to provide a selection of different force vectors to be introduced by the arch wire on the teeth. The holder is separable from the bracket base and is movable relative thereto to permit tipping the arch wire channel and changing its related height between the gingival and occlusal ends of the tooth, and means are provided which releaseably lock the holder in an adjusted position to the bracket base.

6 Claims, 6 Drawing Figures

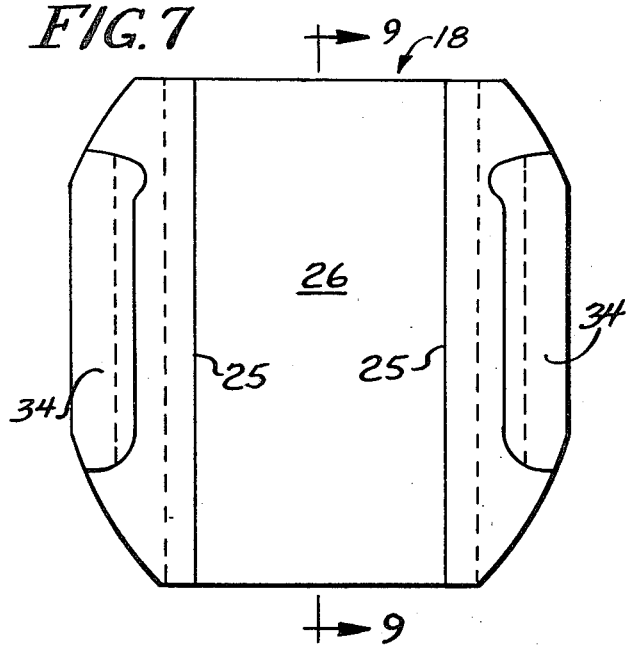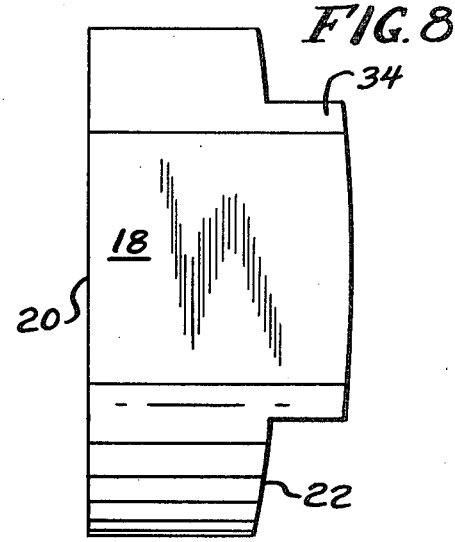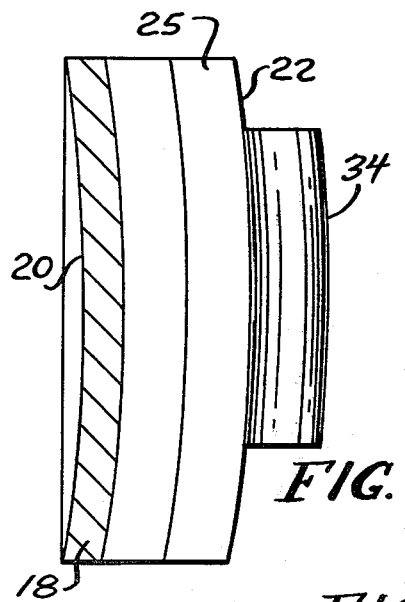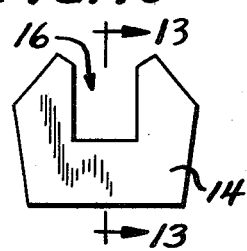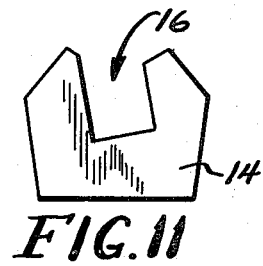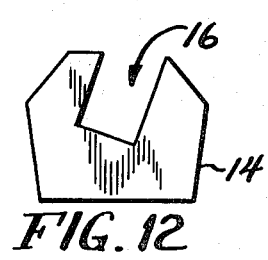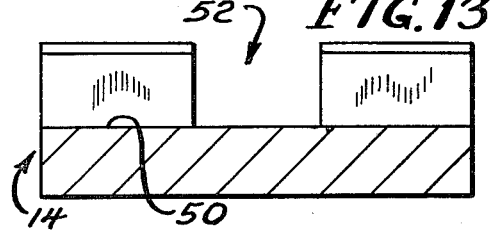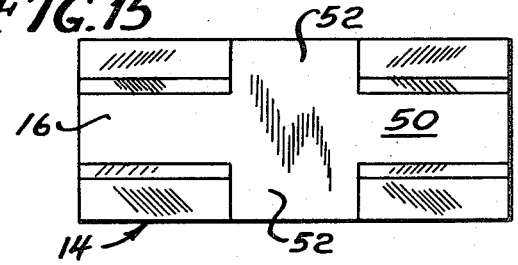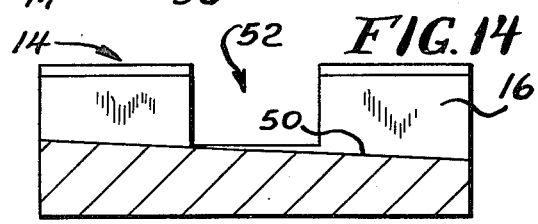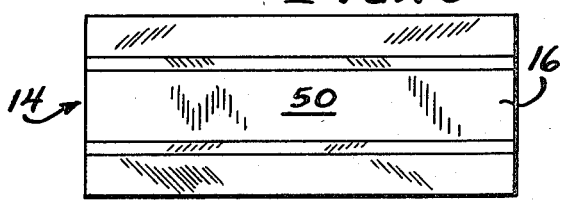

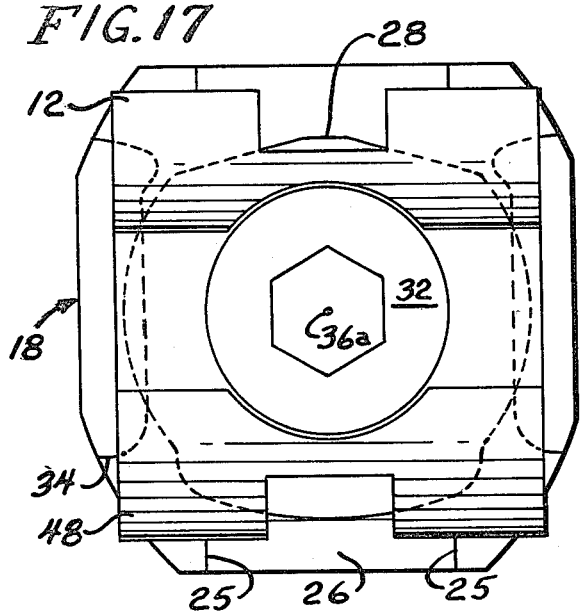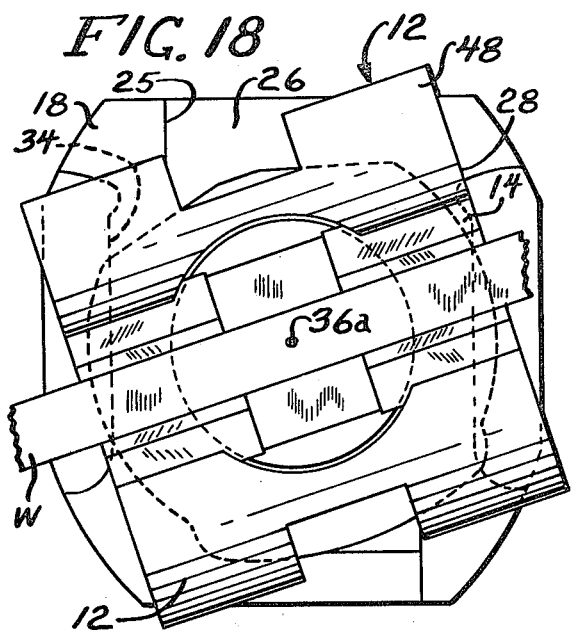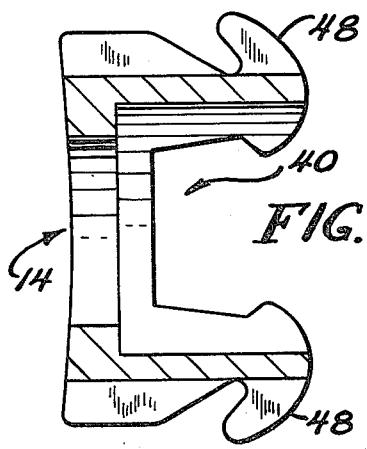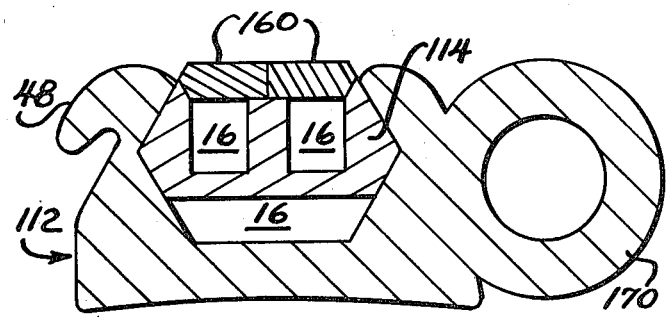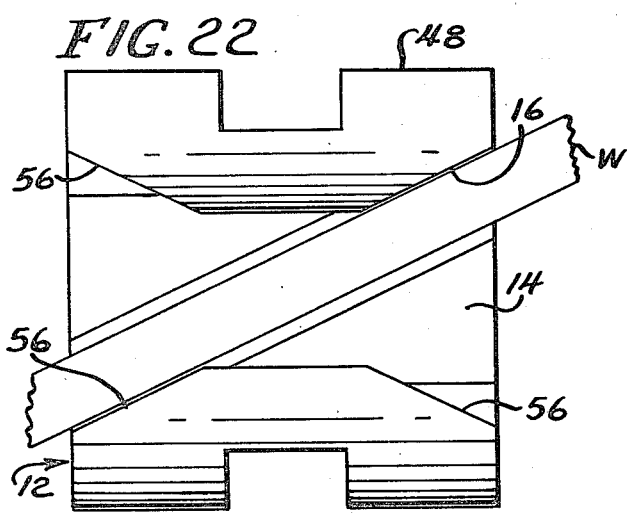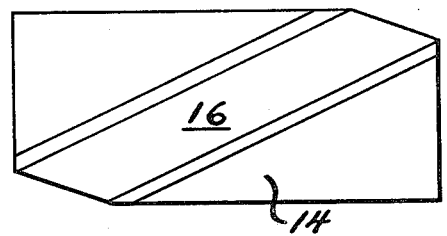

ORTHODONTIC APPLIANCE

This invention relates to orthodontic appliances which employ arch wires in conjunction with brackets to introduce predictable force vectors on a patient's teeth requiring repositioning and/or straightening. More particularly, the invention embodies a novel and improved construction of brackets which facilitate changing and/or adjusting the force vectors and their effect on the teeth to which the brackets are individually fixed.

PRIOR ART AND BACKGROUND

Previously, an orthodontic appliance would include an arch wire which was anchored to teeth on opposite sides of the tooth or teeth to be straightened or repositioned. Usually, metal bands were placed over each tooth to be straightened, and a wire-receiving member or bracket spot-welded to each metal band. In other instances, the wire-receiving member or bracket was adhesively secured directly to the labial or buccal surface of the tooth. The arch wire would be given a bend or twist which would be inserted into the provided receiving channel of each bracket, the bend or twist being relied upon to apply pressure on the tooth in the right direction and in the right amount. Usually, several teeth require movement or straightening; and different angulation or twist of the bends may be required for each tooth. Such technique was not only difficult to make with any assurance that the pressure applied or resulting force vectors would be in the right direction and of the right amount to achieve the sought repositioning of the teeth, but repetition of a predicted force vector was also a problem, particularly where more than one orthodontist was working on the patient's teeth.

Stifter, U.S. Pat. No. 2,908,974, disclosed a bracket intended to improve upon the above-described prior art technique. In said patent, the disclosed bracket comprised an anchor member which is soldered to the metal band and a removable socket or channel member which interfits with the anchor portion. The socket member comprises one of an inventory of interchangeable socket members having wire-receiving sockets or channels which are differently arranged to apply differently directed pressures when the wire is caught therein so that allegedly no predetermined bends are necessary, the shape or inclination of the socket being relied upon to produce the desired vector. Stifter necessarily requires maintenance of a large inventory.

In Andrews, U.S. Pat. Nos. 3,447,128 and 3,660,900, one-piece metal cast brackets are disclosed having a plurality of dimensions built therein which allegedly, when coupled to an unbent arch wire, resulted in predictable force vectors being applied to the tooth. Some eight dimensions were taken into consideration. These included the curvature on the lingual side of the bracket, the radius of the curvature of the arch wire at the point of contact with the individual bracket, plus an angle or inclination which is built into the bracket socket or channel to effect torquing and tipping forces as well as in-out forces and tip compensation and rotation compensation angles as are often required in extraction cases. Such brackets being necessarily cast of one-piece metal, therefore, also require a considerable inventory on the part of the orthodontist in order to meet all force vector requirements with which he must deal in treating his patient. There is also the problem of different tooth sizes and shapes. Mistakes can be corrected only by replacement of the bracket.

SUMMARY OF THE INVENTION

In accordance with the present invention, arch wire and bracket technique in straightening or repositioning mallocated teeth is substantially improved by utilizing an orthodontic bracket comprising a holder which is separable from the base and adapted for non-rotatably supporting a bracket channel member with the slot of the channel extending mesiodistally and open along an exposed side to receive an unbent arch wire portion. The holder and the bracket channel members mounted therein are so designed as to accommodate channel members possessing a wide range of torque angle, for example, in the range of ±50°.

A feature of the invention is that the base and bracket holder are both separable and also adjustable to accommodate occlusal-gingival movement as well as rotational movement of the bracket holder which introduce further variables in the force vectors which the bracket channel member is capable of enforcing on the arch wire inserted into its channel.

A further feature of the invention is that the bracket holder and its bracket channel members can be utilized with a limited inventory of bases which accommodate mounting of the holder and its bracket channel member to differently-sized teeth.

Still another feature of the invention is the large range of torque angle, tipping angle or inclination as well as anti-rotation and in-out angulation or force vectors which can be predictably applied to the tooth on which an orthodontic bracket is mounted and without need to resort to the problematic bent wire technique previously employed.

Still another feature of the invention is that the base of the orthodontic brackets can be mounted on the labial side of the patient's teeth and the bracket holder adjusted relative thereto so as to precisely locate the holder and its channel member in a predictable predetermined position. The result is that the arch wire confined in the bracket channels can be exactly located to impart a predictable force vector.

Still another feature of the invention is that inclination or angulation of the bracket channel is readily adjustable during treatment.

Still another feature of the invention is the means provided which facilitate both straight line occlusal-gingival movement of the holder on the base and rotation through a plane generally paralleling the labial side of the tooth on which the base is fixed to facilitate leveling of the arch wire channel.

A companion feature is the provision of means which releaseably lock the holder with its channel member predictably disposed to introduce the desired torque vectors.

A further feature of the invention is the ability to correct or adjust the tipping angle and/or the occlusal-gingival height of the channel once the bracket is installed on the tooth.

A further feature of the invention is the reduction of inventory of bracket channel members required to be carried by the orthodontist.

Many other objects and feature of the invention will be at once apparent, or will become so upon consideration of the preferred embodiments of the invention which now will be described in connection with the accompanied drawings.

IN THE DRAWINGS

FIG. 7 is a plan view of the bracket base;

FIG. 8 is a mesial or distal view of the bracket base;

FIG. 9 is a vertical sectional view taken of the bracket base along lines 9—9 in FIG. 7 looking in the direction indicated by the arrows;

FIGS. 10, 11 and 12 are cross-sectional views taken through three of an inventory of bracket channel members which are interchangeably assembled in the bracket holder, the arch wire channel being shown inclined at 0° in FIG. 10, at 15° in FIG. 11 and at 30° in FIG. 12;

FIG. 13 is a longitudinal sectional view of a "twin" bracket channel member taken along lines 13—13 of FIG. 10;

FIG. 14 is a view generally similar to FIG. 13 and shows the base of the arch wire channel inclined toward the mesial or distal end of the bracket;

FIG. 15 is a front plan view of a "twin" bracket channel member of either FIG. 13 or 14;

FIG. 16 is a view similar to FIG. 15 and illustrates a "single" bracket channel member;

FIG. 17 is a plan view generally similar to FIG. 3 and shows a second embodiment of the invention wherein the bracket holder and its arch wire channel are adjustable about an axis intersecting the longitudinal axis of the arch wire channel;

FIG. 18 illustrates the holder of a second embodiment adjusted to position its channel at a positive tip angle;

FIG. 19 is a sectional view taken through the bracket holder of said second embodiment;

FIG. 20 illustrates a holder and assembled bracket channel member of a buccal bracket which is adapted to be mounted on one of the patient's molars and serve to anchor the arch wire thereto, the bracket being combined with a buccal tube;

FIG. 21 illustrates an alternative construction of channel member for assembly in the bracket holder of FIG. 20;

FIGS. 22 and 23 illustrate a further embodiment of the invention wherein the channel member contains a predetermined tip angle and the holder is adapted to support such a channel member having a range of tip angles.

DESCRIPTION OF PREFERRED EMBODIMENTS

Figure 1:
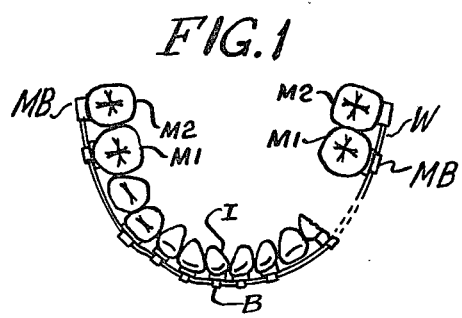
FIG. 1 is a top plan view of a typical orthodontic bracket embodying an arch wire and bracket installation.
Figure 2:
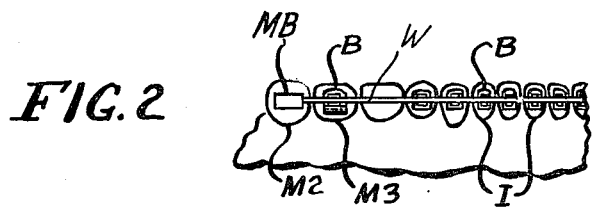
FIG. 2 is a front elevational view thereof.

Referring now more specifically to the several views which comprise the drawings, wherein like parts are identified by like reference numerals, FIGS. 1 and 2 illustrate a typical orthodontic appliance in which the invention has utility. The appliance relies on an unbent arch wire W which is customarily anchored as illustrated by passing its opposed ends through receiving openings in brackets MB which are anchored to molars M1 or M2 at both sides of the patient's jaw. The arch wire W is illustrated as rectangular in cross-section and as substantially filling the corresponding rectangular-shaped channel provided each of the brackets B which are rigidly placed or attached to the labial or buccal side of teeth needing orthodontic treatment. The arch wire, however, may be round in cross section or as not completely filling the rectangular receiving channel. Conventional wire or elastic ligatures (not shown) may be utilized to tie or otherwise retain the unbent arch wire in the receiving channel of each bracket B. The angulation and/or inclination of the bracket channels determine the force vectors introduced by the arch wire to provide the directional guidance required to straighten or move a mal-occluded tooth or teeth (in extraction as well as non-extraction cases) over a period of time to new positions which will improve both occlusion and appearance.

In accordance with this invention, the orthodontic brackets B and MB comprise an assembly 10 as illustrated by FIGS. 3-6 which embodies a holder 12 adapted to removably support one of a set, or inventory, of bracket channel members 14, the channel 16 of which are differently inclined and/or angulated as hereinafter more particularly described. Holder 12, in turn, is separably mounted to a bracket base 18 suitably sized for placement upon the tooth against which the arch wire W in the bracket receiving channel is adapted to apply force vectors.

Considering now also FIGS. 7-9, bracket base 18 is generally square in shape with blunted corners and has parallel disposed anterior and posterior arcuate-shaped surfaces 20 and 22. Preferably, the posterior or lingual-directed side 20 of the separable bracket base 18 is arcuately shaped or cupped to an average of the vertical and horizontal curvatures of the labial side of the incisors or cuspids, or the buccal side in the case of bicuspids or molars, on which the bracket base is adapted to be positioned. Thus, the tooth-attached side 20 of the orthodontic base may be curved along an arc in its mesial-distal dimension so that it closely fits the tooth and assumes a stable position thereon. The tooth-attaching side 20 of the base may be spot-welded to a conventional tooth band (not shown). Alternatively, and preferably, the lingual side of bracket base 18 is adhesively fixed to the labial side of the tooth, as is also conventional. Preferably, the opposite surface 22 of the bracket base on which the bracket holder 12 slides is spherical in shape. However, it may also be planar.

Figure 3:
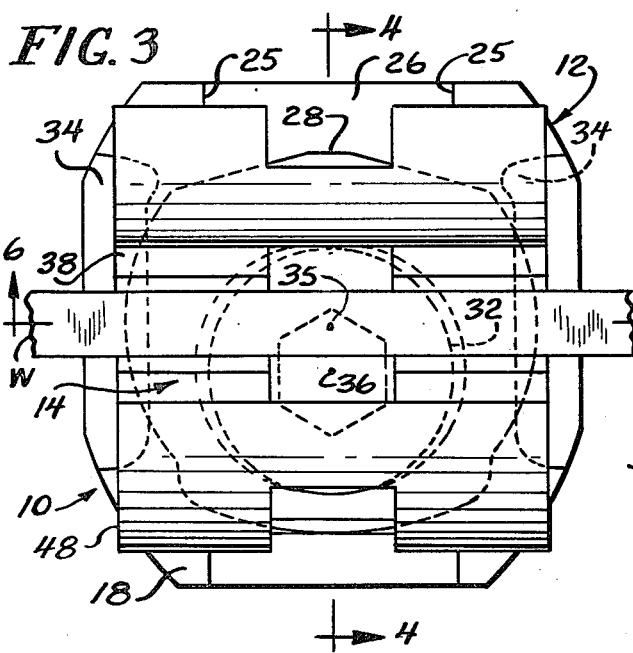
FIG 3 is a front plan view of an orthodontic bracket constructed in accordance with the invention and illustrates an arch wire positioned in the channel thereof.
Figure 4:
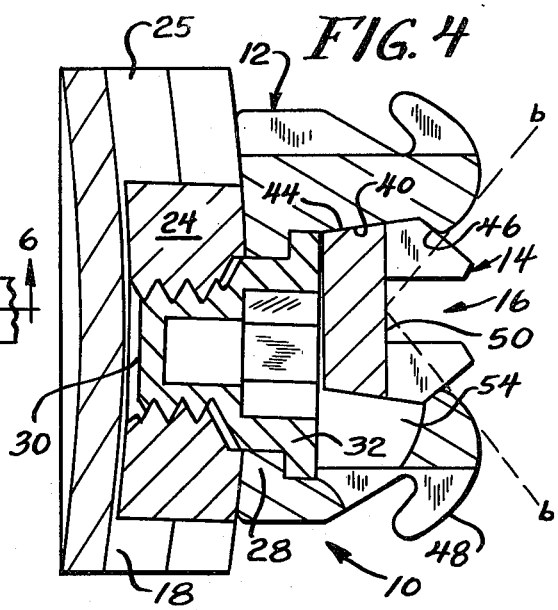
FIG. 4 is a vertical sectional view of the bracket taken along lines 4—4 of FIG. 3 looking in the direction indicated by the arrow.
Figure 6:
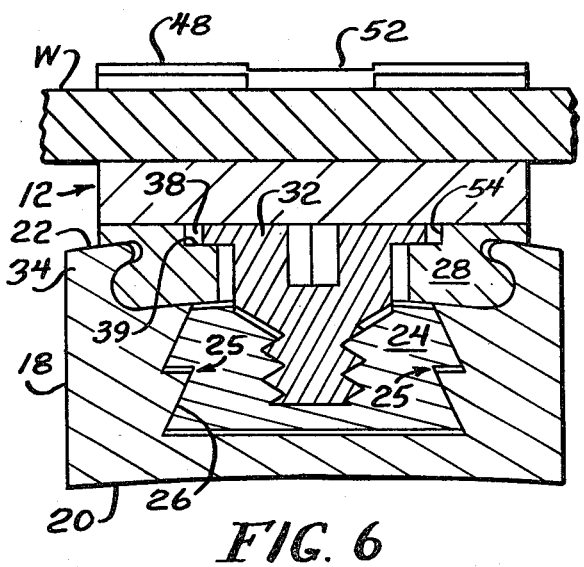
FIG. 6 is a bottom or gingival view of the bracket and is taken at right angles to the view illustrated by FIG. 4.

Considering also FIG. 7 with FIGS. 3, 4 and 6, side 22 of the bracket base 18 has an occluso-gingival extending recessed way 26 in which slide 24 moves toward and away from the occlusal end of the tooth crown to which the bracket base is fixed. A feature is that the mesial and distal side edges of slide 24 have a dovetail shape and interfits with complementing sides 25 of the slideway 26 such that the bracket holder 12 and its channel 16 moves in a predicted direction, e.g., generally parallel to the long axis of the tooth crown when the base is properly fixed in centered relation on the labial side of the tooth.

As shown in FIG. 4, base 28 of the holder 12 is removably fixed to slide 24 by screw 30, the head 32 of which releasably clamps said holder base portion 28 therebetween and slide 24 so that the holder moves with the slide in an occlusal-gingival direction to change the related height of the arch wire receiving groove 16 relative to the arch wire receiving channel of adjacent brackets and can be locked at a desired height by tightening the screw. As illustrated in FIG. 3, the mesial and distal edges of the holder base 28 are confined beneath the wings 34 of the base such that the holder 12 and more specifically its base 28 remains attached to the slide 24 while being free to move therewith toward and away from the occlusal or gingival end of the tooth. Sufficient clearance is also provided to accommodate rotational movement of the holder 12 and its arch wire receiving channel 16 about axis 35. Rotational axis 35 may coincide with the axis 36 of the connecting screw 30. However, in FIG. 3, rotational axis 35 is illustrated as disposed perpendicular to the long axis of the tooth crown on which the bracket is centered and to the occlusal side of the arch wire receiving channel 16.

Figure 5:
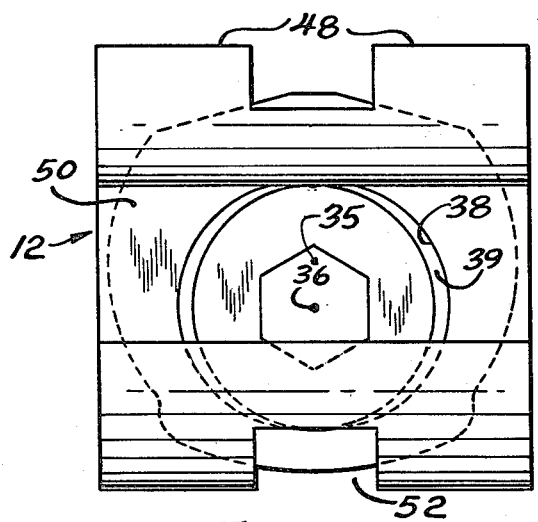
FIG. 5 is a plan view of the holder and is illustrated separate from the bracket base and the bracket channel member with which it is conveniently assembled.

To accommodate rotation of the holder 12 about axis 35, the opening in the base 28 of the holder through which the screw 30 extends is suitably enlarged on its mesial and distal sides affording it a substantially oval shape as illustrated at 38 in FIG. 5 and provided with an appropriate shelf 39 on which the screw head 32 continuously engages. Thus, on loosening of screw 30, the bracket holder 12 and its arch wire receiving channel may be adjusted both occluso-gingivally and also swing about axis 35 while supported on shelf 39 to tip the portion of the arch wire W confined in the bracket channel 16 to a required angle. In the illustrated embodiment, the oval shape of clearance area 38 will permit angulation of the holder about axis 35 through a substantial angle in the order of ±22.5°.

Referring now specifically to FIG. 4, bracket holder 12 is shown provided with a centrally-located mesial-distal extending open-ended groove 40 which is pentagonal in cross-section and serves to non-rotatably support a bracket member 14 of similar pentagonal shape which can be inserted through either the mesial or distal end of said groove 40. As illustrated in FIG. 4, groove 40 of the bracket holder 12 is defined by the upper edge or top surface 42 of the screw 30 which threadedly connects the holder and particularly its base portion 28 to the slide 24. The inner occlusal and gingival sides 44 of said groove 40 diverge outwardly in the labial direction whereas its outer sides 46 diverge inwardly so that similarly-shaped bracket channel member 14 is non-rotatably and rigidly but releaseably secured in the holder 12. Preferably, the holder 12 is provided with gingival and occlusal disposed wings 48 about which ligatures may be tied to secure the wire in bracket channel member 14.

Although other shapes may be provided the bracket channel member 14 and the receiving groove 40 therefor in the bracket holder, the illustrated shape has the advantage of simplicity in manufacture while providing accurate support for the arch wire groove 16 and the reception thereof at different angles of torque. Thus, as illustrated in FIG. 4, sides 46 of the groove 40 are inclined inwardly toward each other and terminate short of each other as to permit a torque angulation of the arch wire receiving channel 16 with limits of ±50° as is indicated at b. In FIG. 10, the arch wire receiving channel 16 is illustrated as set at 0.0 torque angle whereas in FIG. 11, it has been angled at +15° and in FIG. 12, it has been angled at −30°. It will be understood that by mounting the bracket channel member 14 of FIG. 11 in reverse, that a torque angle of −15° may be obtained and similarly, by reversibly mounting the channel member 14 of FIG. 12, the arch wire receiving channel 16 may be given a torque angle of +30°. Also, as illustrated by FIGS. 13 and 14, the base 50 of the arch wire receiving channel of the bracket channel member 14 may be disposed in a plane generally parallel to the tooth surface on which the bracket is mounted or it may be inclined either mesially or distally at an appropriate angle (FIG. 14) to introduce a rotational angle of the force vector exerted on the tooth. Preferably, as illustrated in FIGS. 13-16, the bracket channel member 14 is slotted midway of its distal and medial ends as illustrated at 52.

Referring again to FIG. 4, the bottom wall of the receiving groove 40 in bracket holder member 12 is intentionally omitted through the middle section thereof, and the gingival side thereof is cut out as illustrated at 54 to accommodate insertion and removal of the screw 32 which releaseably connects holder 12 to the slide 24.

From the above, it will be appreciated that in assembling the bracket 10 on the tooth, its base 18 is initially fixed to the labial side of the tooth either by means of a tooth band or adhesively to the labial surface of the tooth. Thereafter, by reaching into the receiving groove 40 with a suitable tool, the screw 30 may be loosened on its connection to the slide 24 to permit adjustment of the bracket toward or away from the gingival edge of the bracket base to locate the channel at an appropriate height. It may be also rotated about rotational axis 35 so as to tip the channel 16 at an appropriate angle. Screw 30 is then tightened to secure the holder and lock it to the holder base 28 in its adjusted position on the base 18.

Referring next to FIGS. 17, 18 and 19, a second embodiment is illustrated wherein the base 28 of the holder 12 is adjustably mounted to the base 18 by means of a similar screw 30 and keyed slide arrangement 24-26, the center of the rotation and thereby the tipping angle of the arch wire receiving channel being this time about axis 36a which coincides with the axis of screw 30 and the arch wire receiving channel along the longitudinal axis thereof at substantially right angles.

FIGS. 22 and 23 illustrates still another embodiment of the invention wherein the holder 12 is adapted to receive a bracket channel member 14 whose arch wire receiving channel 16 is itself inclined at an angle appropriate to provide the proper tipping angle. In order to accommodate a range of angulation, for example, in the order of ±18°, the opposed ends of the holder at the mesial and distal termini of the groove 40 are suitably beveled at 56 to expose the arch wire receiving channel 16 through its full length. It will be appreciated that the holder of FIG. 22 could be rigidly fixed to a base such as illustrated at 18. However, it may also be utilized in an assembly as illustrated in FIGS. 3-6 and 17-19.

Referring next to FIGS. 20 and 21, a somewhat larger-scaled bracket channel member and bracket holder are illustrated at 112 and 114 respectively, the illustrated holder and its illustrated bracket channel members 114 being components of a bracket such as MB aforedescribed as mounted to the buccal side of the molars and serving as anchors for the arch wire. Thus, in FIG. 20, the bracket channel member 114 is shown provided with two rectangular arch wire receiving channels 16 and closed by removable caps 160. FIG. 21 shows a bracket channel member 214 of similar size and shape but having a single centrally-disposed arch wire receiving channel 16 which likewise is removably closed by a cap 260. FIG. 20 further illustrates such a bracket provided with an integrally united buccal tube 170.

From the above description of preferred embodiments of the invention, it will be appreciated that a novel orthodontic appliance utilizing bracket and arch wire technique has been disclosed which is both simple and rugged in construction, and at the same time adding variables which are useful to more precisely control the direction of torque forces exerted against the tooth which the orthodontist may elect to utilize in specific circumstances.

What is claimed is:

1. An orthodontic bracket comprising a base adapted for mounting to the labial or buccal side of a patient's tooth against which a force is to be exerted by means of an arch wire;

a holder slideably mounted on the base containing a mesio-distal extending groove of non-circular cross-section which opens through its opposed ends;

a set of interchangeable members each of a cross-sectional shape complementing that of the groove in the holder and each separably insertable into said recess through one open end thereof so as to be non-rotatably held by the holder;

each said interchangeable members having a longitudinal axis and containing an arch wire receiving channel the disposition of which to said longitudinal axis is different from that of the channel in the other members such that the arch wire when received therein enforces a different force vector on the tooth to which the bracket is mounted;

the holder being slideably mounted on the base to adjust the force vector enforced on the tooth by the arch wire; and means releaseably locking the holder to the base in an adjusted position on the bracket base.

2. The orthodontic bracket of claim 1 wherein the holder is adjustable on the base toward and away from the gingival end of the base.

3. The orthodontic bracket of claim 1 wherein the holder is angularly adjustable on a slide which is keyed to the base to move toward and away from the gingival end of the base, and the locking means releaseably lock the slide and the holder in adjusted relation to the base and slide respectively.

4. The orthodontic bracket of claim 3 wherein the holder is angularly adjustable on the slide about an axis disposed perpendicular to the direction in which the slide moves on the base.

5. The orthodontic bracket of claim 3 wherein the locking means includes a screw which threadedly connects to the slide, the screw head clamping a portion of the holder against the slide when tightened, and the tightening of the screw simultaneously wedging the slide against portions of the base to which it is keyed.

6. An orthodontic bracket as claimed in claim 1 wherein the separable bracket holder is adjustably mounted on a slide which is keyed to the bracket base for gingival and occlusal directed movement, and the bracket base has inwardly facing wings which overly adjacent portions of the holder to maintain the assembly when the locking means is in its released state.

* * * * *